United States Patent [19]

Quenin et al.

[11] Patent Number: 4,948,737

[45] Date of Patent: Aug. 14, 1990

[54] CARTRIDGE FOR PROPERLY RECEIVING TEST ELEMENTS

[75] Inventors: John A. Quenin, Rochester; Mark J. Spath, Spencerport, both of N.Y.

[73] Assignee: Eastman Kodak Company, Rochester, N.Y.

[21] Appl. No.: 293,716

[22] Filed: Jan. 5, 1989

[51] Int. Cl.$^5$ ............................................. G01N 35/00
[52] U.S. Cl. ........................................ 436/46; 422/63; 422/104; 414/795.3
[58] Field of Search ........................... 422/63, 64, 104; 436/46; 353/111, 112, 114, 116, DIG. 1; 414/795.3

[56] References Cited

U.S. PATENT DOCUMENTS

Re. 30,595  4/1981  Covington et al. .
4,159,875  7/1979  Hauser .................................. 356/244
4,273,639  6/1981  Gottermeier .
4,512,952  4/1985  Blanding et al. ...................... 422/63
4,766,714  8/1988  Sugaya .................................. 53/242

FOREIGN PATENT DOCUMENTS 60-55263  3/1985  Japan .

*Primary Examiner*—Robert J. Warden
*Assistant Examiner*—D. John Griffith, Jr.
*Attorney, Agent, or Firm*—Dana M. Schmidt

[57] ABSTRACT

There is described a cartridge for receiving test elements sensitive to improper orientation. A key and keyway are provided on the inside surface of a wall of the cartridge and on the test element in an asymmetric disposition, so that test elements can be inserted only with a proper orientation.

2 Claims, 2 Drawing Sheets

CARTRIDGE FOR PROPERLY RECEIVING TEST ELEMENTS

FIELD OF THE INVENTION

This invention relates to cartridges used to provide test elements to an analyzer to assay sample fluid.

BACKGROUND OF THE INVENTION

Clinical analyzers, be they large, high throughput machines, or smaller, lower throughput machines used in doctor's offices, commonly feature dried test elements for assaying liquids, from cartridges of such test elements. Representative cartridges are shown in U.S. Pat. No. Re. 30,595, especially FIG. 5. Such cartridges are automatically assembled by machine, so that there is little concern for how the test elements are fed into a stack in the cartridge. That is, their proper orientation is assured by quality control maintained by the automated process. Furthermore, many test elements are symmetric in nature in their top surface, that is, have an aperture for deposit of the sample liquid that is symmetrically located on that top surface. Therefore, such elements are somewhat indifferent as to their orientation. However, those shown in, e.g., U.S. Pat. No. 4,273,639, are asymmetric since the two liquid deposit apertures are located at one end only, and spaced away from the longitudinal center line of the test element. These test elements, often used for potentiometric measurements, are very sensitive to proper orientation when they are assembled in the cartridge, for readily apparent reasons. Backwards insertion will, of course, locate the liquid deposit apertures at the wrong end. Upside-down insertion is just as unsatisfactory, since in that case the surface to receive the liquid is no longer the top surface, but underneath. (Each of the elements described in the aforesaid two patents is asymmetric about the center plane that extends parallel to the plane of the element.) Nevertheless, as long as automated equipment assembles such test elements into cartridges, the risk of improper orientation is minimized.

Some analyzers, however, have the operator assemble the test elements into a cartridge by hand, prior to placing the cartridge in the analyzer. Particularly, this is desired if the tests to be run are unique for each patient sample. In such a case, it is not possible to prepackage a variety of different test elements in all the possible combinations that a doctor may wish to test. In these instances of hand loading, the risks of improper orientation rise substantially, particularly if one or more of the test elements happens to be asymmetric as described above.

There has been a need, therefore, prior to this invention, to have a cartridge for test elements that will accept such test elements only in their proper orientation.

SUMMARY OF THE INVENTION

We have constructed a cartridge for test elements, particularly those that are asymmetric, that will accept the test elements only in their proper orientation.

More specifically, in accord with one aspect of the invention there is provided a cartridge for test elements used to assay liquids for analytes. The cartridge comprises wall means for confining the test elements in a stack, a first opening in one of the wall means for inserting a test element to load it into the stack, a second opening in another of the wall means and generally opposite to the first opening, for inserting pusher means for ejecting a test element off of the stack and out through the first opening, and a key or keyway asymmetrically disposed on one of the wall means, for cooperating with a mating keyway or key, respectively, located on test elements in the stack in a matching asymmetric location, whereby the test elements are capable of insertion into the cartridge in one and only one orientation, out of at least four possible orientations.

In accord with another aspect of the invention, there is provided a method of properly orienting in a cartridge a stack of one or more test elements some or all of which include locations for deposition of liquid that are asymmetrically located, the cartridge including wall means for confining the stack, and two generally opposite openings in opposite ones of the wall means, one of the openings being shaped to allow test elements to be inserted into or removed from the stack, the other being shaped to receive pusher means for pushing a test element out of the stack and cartridge. The method comprises the steps of: (a) providing on the test elements in an asymmetric location a keyway or key, (b) providing on one of the wall means a corresponding key or keyway, respectively, shaped and located to mate with the keyway or key of the test element, and (c) loading the test elements into the cartridge so that the keyway or key of the test element aligns and mates with the key or keyway of the cartridge.

Accordingly, it is an advantageous feature of the invention that a cartridge is provided that will accept a test element to load it in a stack of one or more elements, only if the test element is properly oriented.

It is a related advantageous feature of the invention that a test element improperly oriented cannot be loaded into a cartridge of this invention.

Other advantageous features will become apparent upon reference to the following description of the preferred embodiments, when read in light of the attached drawings.

DESCRIPTION OF THE PREFERRED EMBODIMENTS

The invention is described in connection with its preferred embodiments. For example, it is shown with respect to test elements of a preferred type, wherein a keyway is formed on each test element and a key on a wall surface of the cartridge. In addition, the invention is useful with test elements of any type having any chemistry for any assay, and whether the key is on the cartridge or on the test element. (If the key is on the test element, protruding therefrom, then a corresponding keyway is formed in the appropriate wall surface of the cartridge.) In addition, the invention is useful if the test elements are rectangular, as shown, or if they are any other shape such as square.

Figure 1:
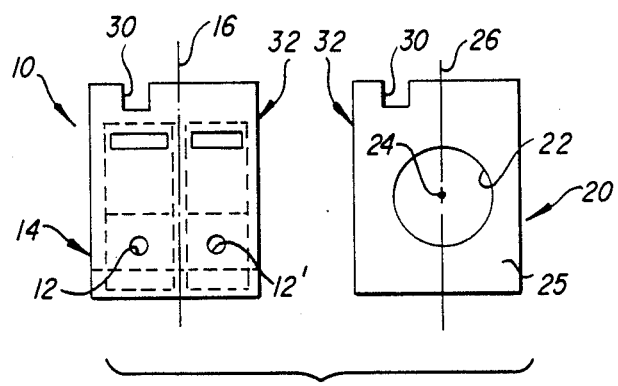
FIG. 1 is a side-by-side plan view of two different kinds of test elements that can be loaded in a cartridge of this invention.

As shown in FIG. 1, there are generally two kinds of test elements 10, 20 useful with the invention. Type 10 is an asymmetric type, having two liquid deposit apertures 12, 12' that are located at one end 14 of the element, either side of the longitudinal center line 16 that extends the length of the test element. Examples of such elements are shown in the aforesaid U.S. Pat. No. 4,273,639, so that further details are unnecessary.

Type 20 is a more symmetric type, for example, a conventional colorimetric type, that has a single liquid-deposit aperture 22 located so as to be centered (at 24) on the longitudinal center line 26 that runs the length of test element 20. However, it is asymmetric insofar as aperture 22 is only located in the top surface 25, and not underneath. The same is true of type 10.

Such test elements have conventionally included, for both types, a notch 30 located at ends 32 of the test element off to the side from center lines 16 and 26. Prior to this invention, these notches have been used exclusively for orienting the parts of the test element only DURING manufacturing, and not thereafter. They had not provided any use in the cartridges which have held them.

Figure 2:
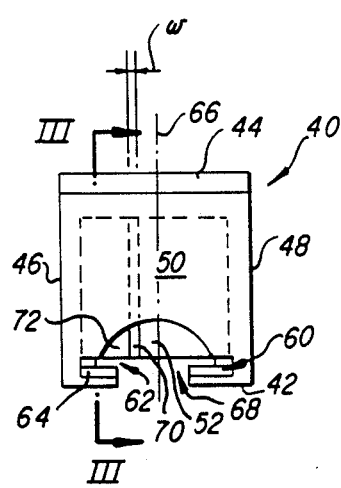
FIG. 2 is an end elevational view of a cartridge constructed in accordance with the invention, the spring biasing means and test elements having been omitted for clarity.
Figure 3:
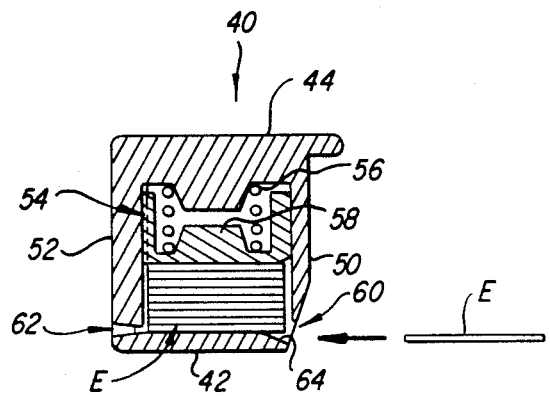
FIG. 3 is a section view taken generally along line II—II of FIG. 2, and showing the cartridge fully loaded.

In accordance with the invention, a cartridge 40, FIGS. 2 and 3, is provided that will accept any of the test elements 10 or 20 only if they are properly oriented. Cartridge 40 preferably comprises opposite end walls 42, 44, and two pairs of opposing side walls 46, 48 and 50, 52, and biasing means 54 for biasing test elements against end wall 42, FIG. 3. Preferably biasing means 54 comprises a compression spring 56 and a cylindrical platen 58. Alternatively, not shown, a weighted platen can be used without a spring. Side wall 50 includes an opening 60 shaped to allow test elements to be fed by hand into the cartridge, and to be ejected by the analyzer. In opposite side wall 52 there is an opening 62 that is opposite and generally aligned with opening 60, to allow a pusher blade (not shown) to enter the cartridge to eject a test element out of opening 60. Opening 62 is not large enough to allow a test element to pass through. A ramp 64 is preferably provided on end wall 42 at opening 60 to assist in guiding test elements into the stack against the action of biasing means 54.

Cartridge 40 includes a longitudinal center line 66, FIG. 2, that generally defines a plane in which the longitudinal center lines of test elements E, FIG. 3, coincides. Such elements are usually a mixture of types 10 and 20.

To insure the test elements are inserted with the proper orientation, a key 70 is provided protruding from inside surface 72 of wall 52, as best seen in FIG. 2. Key 70 is a rib positioned to fit into and mate with notches 30 of test element 10 or 20 if and only if those elements are fed in with end 32 going in first and with the proper (metering) side up. Thus, notches 30 function as keyways. (A notch similar to notch 30 is also preferably formed in platen 58, not shown.) Because the test elements are not square, the key and keyway are not needed to preclude the test elements from being improperly inserted turned 90° from their proper orientation. (However, the key and keyway construction would also be useful to prevent such misorientation if square test elements were used.) As such, therefore, there are four possible insertions of test elements 10 and 20, only one of which can succeed: The permitted one is right-side up with end 32 in first, since in that case notch 30 mates with key 70. The impermissible ones are right-side up with end 32 in last, in which case notch 30 is at the opposite, wrong end for mating with key 70; upside down with end 32 in last so that again notch 30 is at the wrong end; or upside down with end 32 in first, in which case notch 30 is on the opposite, non-mating side of centerline 16. Visual inspection of the cartridge indicates whether each test element has been properly loaded.

Optionally, end wall 42 includes a slot 68, FIG. 2, which allows the interior of the incubator to be viewed from underneath. The operator or person loading the cartridge can check on the mating of the key and keyway by viewing through this slot.

Figure 4:
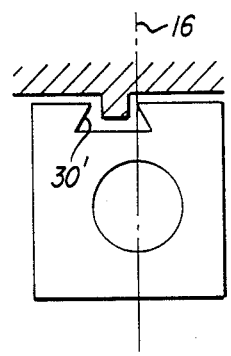
FIG. 4 is a fragmentary plan view, partly in section, showing an alternative embodiment of the key and keyway of the invention.

The actual shapes of key 70 and the notch 30 are shown as being rectangular, but any mating shape is useful, for example, a triangular shape to produce a key with a pointed ridge. It will be readily apparent that notch 30 needs to have an opening that will accommodate the width "w" of the key, FIG. 2, so that even non-congruent shapes 30' can be used if they still mate with the key, for example as shown in FIG. 4.

Figures 5A, 5B:
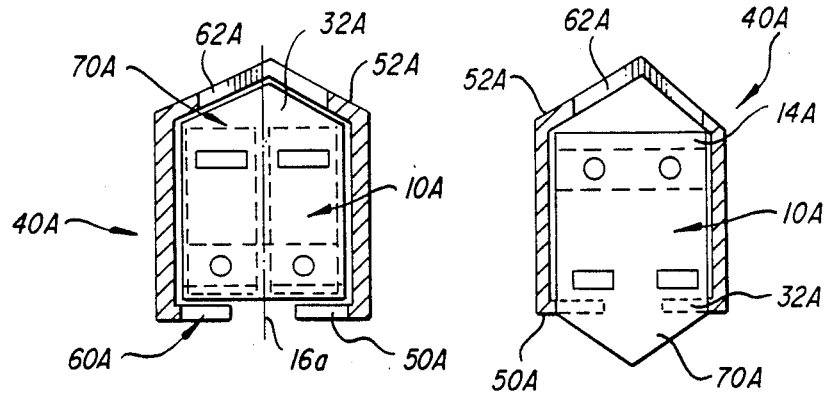
FIGS. 5A and 5B are section views of an alternate embodiment of the cartridge, taken through the opposed openings in the side walls.

Furthermore, the key or keyway need not be a feature in or on side wall 52. For example, it can be the entire side wall, as shown in FIGS. 5A and 5B. Parts similar to those previously described bear the same reference numeral, to which the distinguishing suffix "A" has been added. Thus, cartridge 40A receives test elements such as element 10A, through opening 60A in side wall 50A, as in the previous embodiment. Opening 62A is used to push out test elements as they are needed. However, the test elements in this embodiment have a key 70A built onto end 32A, as the entire end feature thereof. Instead of side wall 52A having a notch in one part of it to receive the key, the entire side wall 52A is shaped to receive the key, FIG. 5A. If, however, end 14A were to be put in first, FIG. 5B, element 10A cannot fit and the operator is alerted to the error. (Alternately, wall 52A can be folded in to form the key, with a notch on element 10A.) Preferably, the point of wall 62A, as well as of the key 70A on the test element, is asymmetrically located with respect to center line 16A, as shown, to prevent the test element from being inserted upside down.

Figure 6:
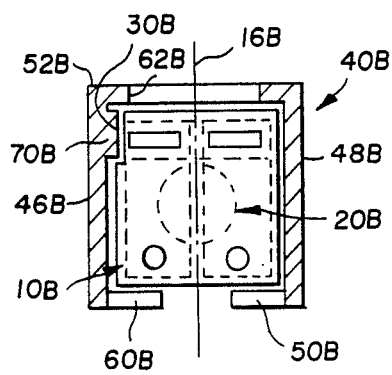
FIG. 6 is a section view similar to that of FIG. 5A, but illustrating yet another embodiment.

Another example of the cartridge key not being a feature of wall 52 is illustrated in FIG. 6, wherein similar parts are shown with the same reference numeral with the letter "B" added. Thus, cartridge 40B receives test elements such as elements 10B through opening 60B in side wall 50B, and a pusher blade extends through opening 62B in side wall 52B to push them out, as before. However, key 70B is now a rib that is part of side wall 46B (or alternatively 48B, not shown), which is an asymmetric location with respect to center line 16B of the elements. Each test element 10B (or 20B, shown in phantom) is provided with a matching notch 30B cut into the appropriate corner of the test element. In such a design, the test element width must be sufficient to accommodate both the notch and the portions providing the testing function.

The invention has been described in detail with particular reference to preferred embodiments thereof, but it will be understood that variations and modifications can be effected within the spirit and scope of the invention.

What is claimed is:

1. A method of properly orienting in a cartridge a stack of one or more test elements some of which can include locations for deposition of liquid that are asymmetrically located, the cartridge including wall means for confining the stack, and two generally opposite openings in opposite ones of said wall means, one of said openings being shaped to allow test elements to be inserted into and removed from the stack, the other being shaped to receive pusher means for pushing a test element out of the stack and cartridge; the method comprising the steps of:

(a) providing on said test elements in an asymmetric location a keyway or key, (b) providing on one of said wall means other than the one having said one opening, a corresponding key or keyway, respectively, shaped and located to mate with the keyway or key of the test element, and (c) loading the test elements into the cartridge through said one opening one at a time so that the keyway or key of the test element aligns and mates with the key or keyway of said cartridge, respectively.

2. A method as defined in claim 1, wherein said loading step includes the step of inserting each following test element under the preceding test element to create a stack of test elements having the most recent member of the elements at the bottom.

* * * * *